(12) United States Patent
Hein et al.

(10) Patent No.: US 7,769,129 B2
(45) Date of Patent: Aug. 3, 2010

(54) X-RAY COMPUTED TOMOGRAPHY APPARATUS

(75) Inventors: Ilmar A. Hein, Chicago, IL (US);
Aleksandr A. Zamyatin, Buffalo Grove, IL (US)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 57 days.

(21) Appl. No.: 12/326,341

(22) Filed: Dec. 2, 2008

(65) Prior Publication Data
US 2010/0034344 A1    Feb. 11, 2010

(30) Foreign Application Priority Data
Aug. 5, 2008    (JP) .............................. 2008-202013

(51) Int. Cl.
H05G 1/60 (2006.01)
(52) U.S. Cl. ...................................................... 378/19
(58) Field of Classification Search ................ 378/4, 378/5, 9, 19, 901
See application file for complete search history.

(56) References Cited
U.S. PATENT DOCUMENTS

| | | | | |
|---|---|---|---|---|
| 5,173,852 A | | 12/1992 | Lonn | |
| 5,590,164 A | * | 12/1996 | Kawai et al. | 378/4 |
| 6,047,040 A | * | 4/2000 | Hu et al. | 378/19 |
| 7,062,006 B1 | * | 6/2006 | Pelc et al. | 378/9 |
| 7,639,775 B2 | * | 12/2009 | DeMan et al. | 378/9 |
| 2003/0123614 A1 | * | 7/2003 | Silver et al. | 378/146 |

* cited by examiner

Primary Examiner—Irakli Kiknadze
(74) Attorney, Agent, or Firm—Oblon, Spivak, McClelland, Maier & Neustadt, L.L.P.

(57) ABSTRACT

An X-ray computed tomography apparatus includes an X-ray tube (101) which generates X-rays, a multi-channel X-ray detector (103) which detects X-rays transmitted through an object to be examined, a rotating frame (102) which is equipped with the X-ray tube and the X-ray detector, a reconstruction unit (114) which reconstructs an image on the basis of an output from the X-ray detector, and a control unit (121) which alternately shifts the X-ray focal spot of the X-ray tube along the rotating direction on the anode by a distance +σ and a distance −σ for each view. The distance σ is set to $$\sigma = SOD \cdot \tan\left(\frac{\Delta\beta}{2}\right)$$

where SOD is the distance between the X-ray tube and the rotation center, and Δβ is the angle difference between adjacent views, such that X-ray focal spots in the adjacent views overlap each other at almost the same position.

8 Claims, 6 Drawing Sheets

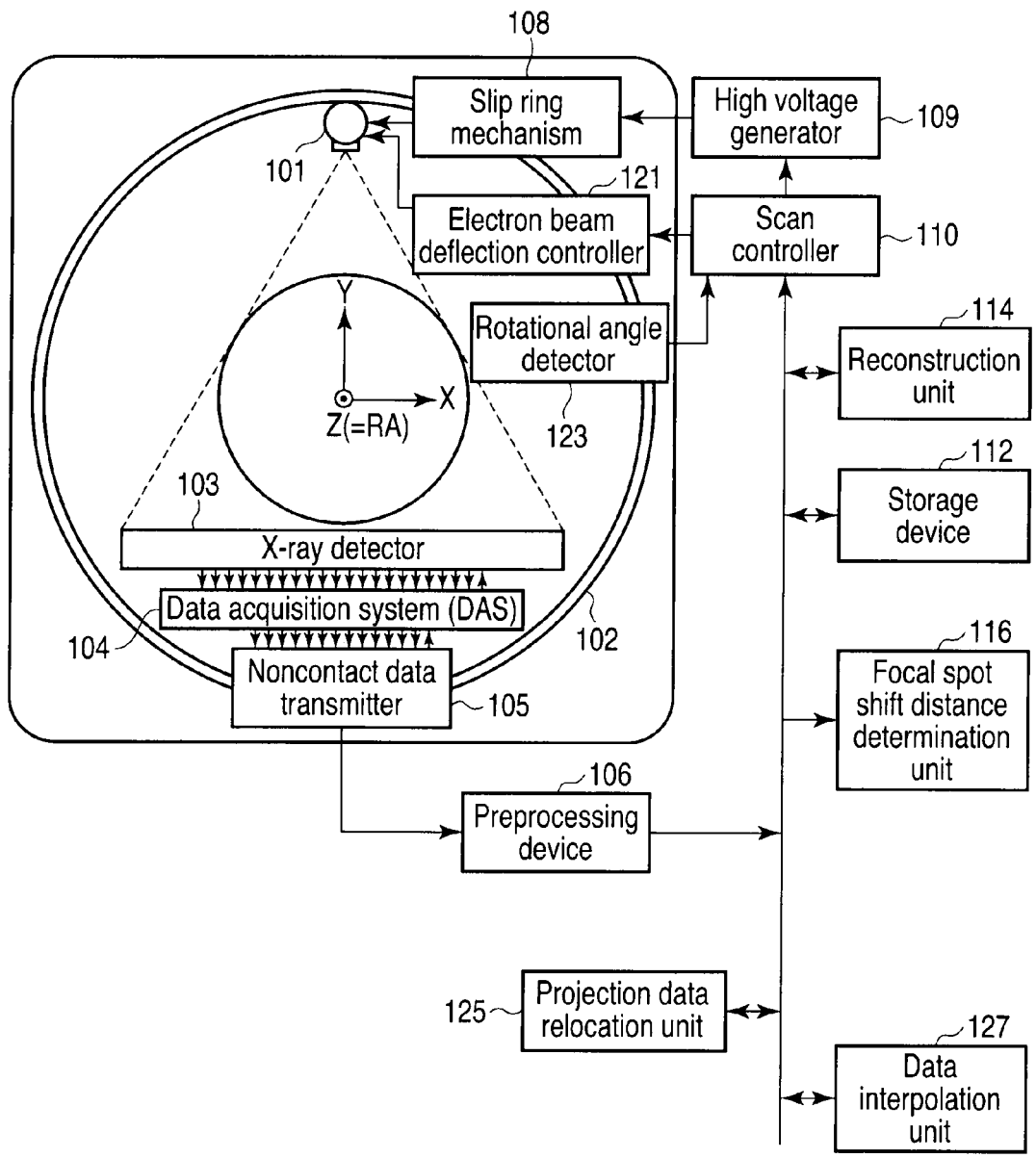
F I G. 1

X-RAY COMPUTED TOMOGRAPHY APPARATUS

CROSS-REFERENCE TO RELATED APPLICATIONS

This application is based upon and claims the benefit of priority from prior Japanese Patent Application No. 2008-202013, filed Aug. 5, 2008, the entire contents of which are incorporated herein by reference.

BACKGROUND OF THE INVENTION

1. Field of the Invention

The present invention relates to an X-ray computed tomography apparatus.

2. Description of the Related Art

Using a flying focal spot (FFS) X-ray tube capable of electromagnetically moving an X-ray focal spot generated on the anode can improve the spatial resolution of X-ray CT. If the rotational axis direction of X-ray CT is the Z direction, deflecting electron beams in the axial (z) direction and a lateral (x-y) direction perpendicular to it can improve the spatial resolutions in the directions.

The conventional lateral FFS method has two drawbacks. The first drawback is that it is necessary to relocate an X-ray beam having an original conical beam shape so as to apply the beam as a parallel X-ray beam and to perform resampling. The second drawback is that the spatial resolution in the x-y direction becomes uneven throughout an effective field of view.

FIG. 8 shows a conventional FFS technique used to improve the spatial resolution in the lateral (x-y) direction. The pitch angle of an X-ray detector can be equivalently set to $\Delta\gamma/2$ by alternately moving the focal spot in the lateral direction by $\pm\sigma_{FFS}$. In this case, $\sigma_{FFS}$ is given by $$\sigma_{FFS} = \frac{\Delta\gamma \cdot SOD \cdot SDD}{4 \cdot (SDD - SOD)} \quad (1)$$

where SOD is the distance between the X-ray tube and the rotation center (isocenter), and SDD is the distance between the X-ray tube and the X-ray detector.

While a focal spot alternately moves from $+\sigma_{FFS}$ to $-\sigma_{FFS}$ at a high speed for each view (irradiation field of view), the detector can be regarded as remaining at almost the "same" position. In the rotation center (isocenter), the detector corresponding to the first position of the X-ray tube is equivalently shifted from the detector corresponding to the second position of the X-ray tube by 0.5 channel. This doubles the sampling density.

Unfortunately, the conventional algorithm cannot be applied to a conical beam arrangement. Since the positional relationship between the X-ray tube and the X-ray detector differs for two views, directly interlacing channel data as outputs from the detector will cause ripples in the projection data obtained by interlacing. Such ripples result in artifacts in reconstructed images. Ripples can be removed by filtering. This, however, may decrease the spatial resolution in the x-y direction and spoil the object of FFS, i.e., an improvement in spatial resolution. The conventional FFS algorithm solves this problem by re-binning and re-sorting data from a conical beam arrangement to a parallel beam arrangement. This process requires much time for calculation. In addition, re-sampling included in re-binning and re-sorting imposes a limitation on the possible improvement of the spatial resolution in the x-y direction.

A further drawback of the conventional algorithm is that since the sampling density is doubled only in the rotation center (isocenter) in a strict sense, the spatial resolution in the x-y direction becomes uneven throughout the effective field of view. Re-binning and re-sorting for a parallel beam arrangement cannot provide any measures against this problem.

BRIEF SUMMARY OF THE INVENTION

It is an object of the present invention to uniformly improve the spatial resolution throughout the effective field of view in the lateral (X-Y) direction on the basis of projection data obtained with an original conical beam arrangement by properly setting a flying focal spot (FFS) position without relocation or re-sampling of the projection data.

According to the present invention, there is provided (claim 1)

According to the present invention, the spatial resolution can be uniformly improved throughout the effective field of view by using projection data acquired with an original conical beam arrangement without relocation or re-sampling of the projection data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing the arrangement of an X-ray computed tomography apparatus according to an embodiment of the present invention;

DETAILED DESCRIPTION OF THE INVENTION

Figure 2:
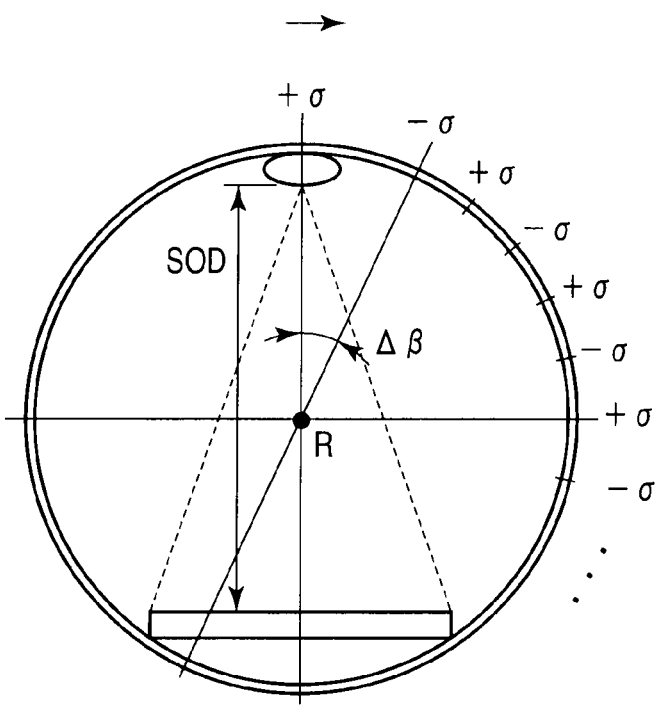
FIG. 2 is a view showing shift control on an X-ray focal spot by a balanced flying focal spot method according to this embodiment.

An embodiment of the present invention will be described below with reference to the views of the accompanying drawing.

FIG. 1 shows the internal structure of the gantry of an X-ray computed tomography apparatus according to this embodiment with the front cover of the gantry housing being removed. A gantry 100 includes an X-ray tube 101.

The X-ray tube 101 has a deflecting coil which deflects an electron beam from the cathode to the rotating anode which is an umbrella-like target by magnetic force. The electron beam is deflected by magnetic force, and an X-ray focal spot on the rotating anode shifts within the x-y plane. An electron beam deflection controller 121 dynamically controls the shift of this X-ray focal spot. In this case, assume that the rotational axis direction of a rotating frame 102 is defined as a z-axis, and the x-y plane is defined as a plane perpendicular to the rotational axis z.

The X-ray tube 101 receives a tube voltage and a filament current from a high voltage generator via a slip ring mechanism 108, and generates an X-ray cone beam. The X-ray tube 101 is mounted, together with an X-ray detector 103, on the rotating frame 102 supported to be rotatable about a rotation axis RA (equivalent to the z-axis). A rotational angle detection unit 123 is provided to detect the rotational angle of the rotating frame 102. In general, when the X-ray tube 101 is at the vertex, the rotational angle of the rotating frame 102 is set to 0°. The X-ray detector 103 faces the X-ray tube 101 through the rotation axis RA. A cylindrical imaging area is provided centered on the rotation axis RA, and an object to be examined is placed in the imaging area. The X-ray detector 103 detects X-rays emitted from the X-ray tube 101 and transmitted through the object. The X-ray detector 103 is of a multi-slice type or two-dimensional array type corresponding to a cone beam. That is, the X-ray detector 103 has a plurality of X-ray detection element arrays arranged parallel along the rotation axis RA. Each X-ray detection array has a plurality of X-ray detection elements arrayed in a line along a direction perpendicular to the rotation axis RA.

A data acquisition system (DAS) 104 amplifies an output from the X-ray detector 103 for each channel, and converts the amplified output into a digital signal. The signal is then sent to a preprocessing device 106 via, for example, a non-contact data transmitter 105. The preprocessing device 106 performs correction processing such as sensitivity correction for the signal, and stores the resultant data as so-called projection data at a stage immediately before reconstruction processing in a storage device 112. A scan controller 110 controls a rotation driving unit, a high voltage generator 109, the data acquisition system 104, and the like for data acquisition (scanning).

The electron beam deflection controller 121 discretely shifts an X-ray focal spot generated on the rotating anode of the X-ray tube 101 at a high speed. The absolute values of the shift distances of X-ray focal spots in adjacent views are made equal to each other. As shown in FIG. 2, however, X-ray focal spots are shifted in opposite directions in adjacent views. A focal spot shift distance determination unit 116 determines a shift distance o such that X-ray focal spots overlap each other at almost the same position in adjacent views. Letting SOD be the distance between the X-ray tube 101 and the rotation axis RA, and $\Delta\beta$ be the angle difference between adjacent views, the shift distance σ is determined as follows:

$$\sigma = SOD \cdot \tan\left(\frac{\Delta\beta}{2}\right) \quad (5)$$

The angle difference $\Delta\beta$ between adjacent views is determined based on an X-ray spread angle $\Delta\gamma$ corresponding to one channel of the X-ray detector 103. A projection data relocation unit 125 is provided to relocate the projection data of adjacent views in which X-ray focal spots overlap each other at almost the same position into the projection data of a single view. The projection data of a single view is generated from the projection data of two adjacent views in which X-ray focal spots overlap each other at almost the same position. Setting the focal spot shift distance determined according to the above equation can double the spatial resolution of the projection data of a single view which is generated from the projection data of two adjacent views. A data interpolation unit 127 interpolates a peripheral portion of projection data which can use only incomplete data of a single view which is relocated by the projection data relocation unit 125. A reconstruction unit 114 reconstructs the data of a tomogram on the basis of a set of interpolated projection data of the single view. One set covers 360° or 180°+a fan angle.

This embodiment has two characteristic features. That is, the embodiment (1) can obviate the necessity of re-binning or re-sorting for a parallel beam arrangement by directly interlacing (combining) channel data in an original cone beam arrangement without any artifact, and (2) can obtain a uniform spatial resolution in the lateral direction throughout an effective field of view.

Figure 3:
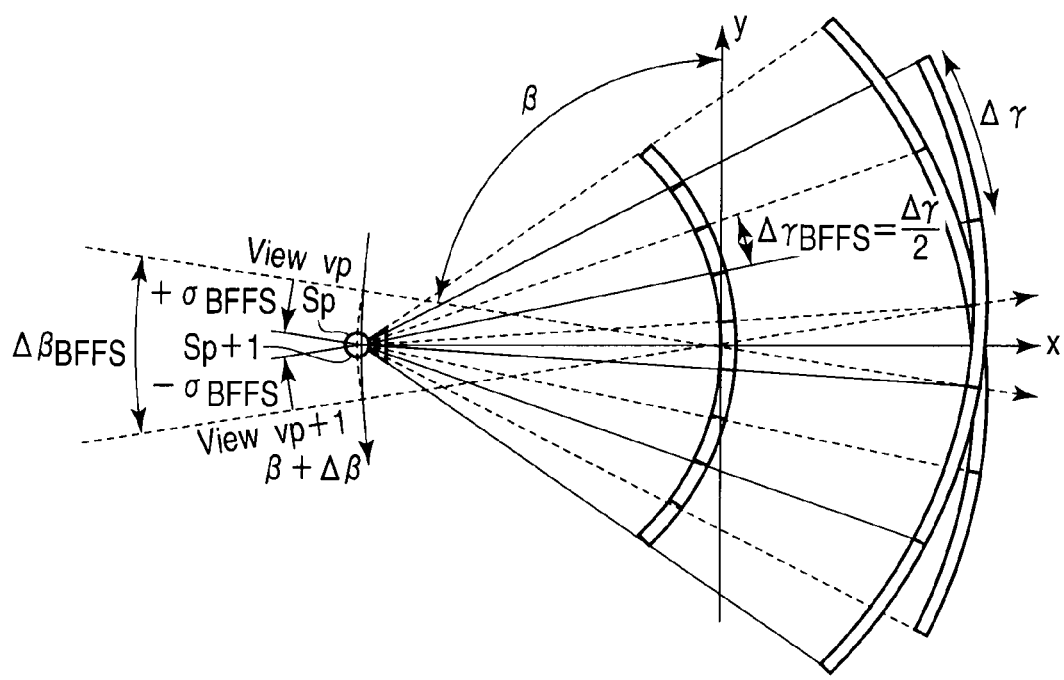
FIG. 3 is a view showing the shift direction and distance of each X-ray focal spot in this embodiment, wherein an image obtained by applying X-rays in a view $v_p$ and an image obtained by applying X-rays in a view $v_p+1$ are superimposed and displayed when viewed from the middle point (X-ray tube position)

In addition, this embodiment is based on a balanced flying focal spot (BFFS) arrangement and algorithm. The embodiment (1) determines a deflection distance by calculation so as to keep the focal spot position of the X-ray tube instead of the detector at the same position in two adjacent views, and (2) calculates an angle difference $\Delta\beta_{BFFS}$ between views such that an angle interval $\Delta\gamma_{BFFS}$ of interlaced X-ray beams accurately becomes $\Delta\gamma/2$ at an arbitrary position located out of the central axis as well as in the rotation axis RA (isocenter). This will be described with reference to FIG. 3. A focal spot is deflected to position $xy_{fs}=+\sigma_{BFFS}$ on the X-Y plane in a view $v_p$ and to position $xy_{fs}=-\sigma_{BFFS}$ in a view $v_p+1$, and the view angle between the two positions is obtained as $\Delta\gamma_{BFFS}$.

$$\sigma_{BFFS} = SOD \cdot \tan\left(\frac{\Delta\beta_{BFFS}}{2}\right) \quad (2)$$

$$\Delta\beta_{BFFS} = \sin^{-1}[M \cdot \Delta\gamma \cdot (n+0.5)]; n \text{ integer} \quad (3)$$

$$M = \frac{SDD}{SDD - SOD} \quad (4)$$

When $\sigma_{BFFS}$ and $\Delta\gamma_{BFFS}$ are calculated according to equations (1) to (3), X-ray tube positions $S_p$ an $S_p+1$ become the same, and X-ray beams to be interlaced are spaced apart from each other accurately by $\Delta\gamma/2$.

Note that the scan controller 110 can change the scan speed (the time required for one rotation). The scan controller 110 can also change the number of views per rotation (VPR) by changing the sampling rate of the DAS 104 in accordance with the scan speed. The following is a typical example. In this case, n is defined as "the value obtained by subtracting 0.5 from the channel difference for the views $v_p$ and $v_p+1$ when they are converted into channels to be interlaced". VPR can be changed as follows:

When n=0, VPR=5777.
When n=1, VPR=1926.
When n=2, VPR=1155.
When n=3, VPR=825.
When n=4, VPR=642.
When n=5, VPR=525.

At the maximum rotational speed of the gantry, n=5 is selected. As the rotational speed decreases, n is set to be closer to 0. This can make full use of a resource called a data transfer rate which tends to be bottleneck of the performance of the X-ray computed tomography apparatus.

(Focal Spot Deflection and View Angle Difference)

Figure 4:
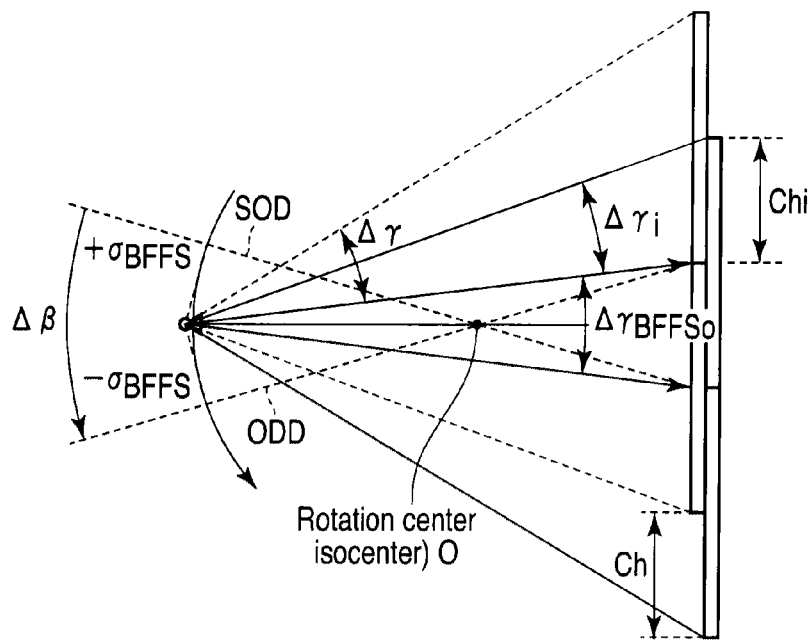
FIG. 4 is a view for explaining a situation in which a bend in a detector can be neglected in a balanced flying focal spot technique according to this embodiment.

A shift distance σ of a BFFS is obtained on the basis of FIG. 4. The following description is based on two assumptions, i.e., that the degree of bend in the detector can be neglected and that the relative inclination angle between detectors corresponding to +σ and −σ can be neglected. In general, a focal spot position can be obtained by $$\sigma = SOD \cdot \tan\left(\frac{\Delta\beta}{2}\right) \tag{5}$$

The angle between the central axes of X-ray beams in two views is represented by $\Delta\gamma_{BFFSo}$ given by $$\gamma_{BFFSo} = 2\tan^{-1}\left[\frac{ODD \cdot \cos\frac{\Delta\beta}{2} \cdot \sin\frac{\Delta\beta}{2}}{SOD + ODD \cdot \cos^2\frac{\Delta\beta}{2}}\right] \approx 2\tan^{-1}\left[\frac{\sin\Delta\beta}{2M}\right] \tag{6}$$

where ODD is the distance between the rotation center (isocenter) and the detector, and M is the geometric factor defined by equation (4).

An angle $\Delta\gamma_i$ between X-ray beams to be interlaced takes a value between 0 and $\Delta\gamma$ as $\Delta\beta$ and $\Delta\gamma_{BFFSo}$ change. $\Delta\gamma_i$ is given by $$\Delta\gamma_i = \Delta\gamma \cdot FRAC\left[\frac{\Delta\gamma_{BFFSo}}{\Delta\gamma}\right] (0 \leq \Delta\gamma_i < \Delta\gamma) \tag{7}$$

The function "FRAC" used in this equation is designed to output only the decimal part of the number in the brackets. By normalizing $\Delta\gamma_i$ and $\Delta\gamma_{BFFSo}$ using $\Delta\gamma$ for each channel, the following amounts can be defined:

$$\Delta Ch = \frac{\Delta\gamma_{BFFSo}}{\Delta\gamma} \tag{8}$$

$$\Delta Ch_i = \frac{\Delta\gamma_i}{\Delta\gamma} \tag{9}$$

where $\Delta Ch$ is the amount by which one detector shifts from another detector on a channel basis, and $\Delta Ch_i$ is the overlap amount between channels. Solving the equation with respect to $\Delta\beta$ can obtain $$\Delta\beta = \sin^{-1}\left[2M\tan\left(\frac{\Delta Ch \cdot \Delta\gamma}{2}\right)\right] \approx \sin^{-1}[M \cdot \Delta Ch \cdot \Delta\gamma] \tag{10}$$

A desired X-ray beam interlacing angle is given by $$\Delta\gamma_i = \frac{\Delta\gamma}{2} \tag{11}$$

-continued $$\Delta\gamma_{BFFSo} = \Delta\gamma(n + 0.5); n \text{ interger} \tag{12}$$

$$\Delta Ch_i = 0.5 \tag{13}$$

$$\Delta Ch = n + 0.5 \tag{14}$$

Combining equations (10) and (14) will lead to balanced flying focal spot $\Delta\beta_{BFFS}$ equation (3).

An integer n and corresponding $\Delta Ch$ are selected to make the number of views $VPR_{Acq}$ per rotation become a practical number of views. Letting $\Delta\beta$ be an angle ranging from the rotation center to the views $v_p$ and $v_p+1$, the angle is given by $$VPR_{Acq} = \frac{360}{\Delta\beta} \tag{15}$$

Note that $\Delta\beta$ is expressed by the circular measure.

(BFFS Reconstruction)

Figure 5:
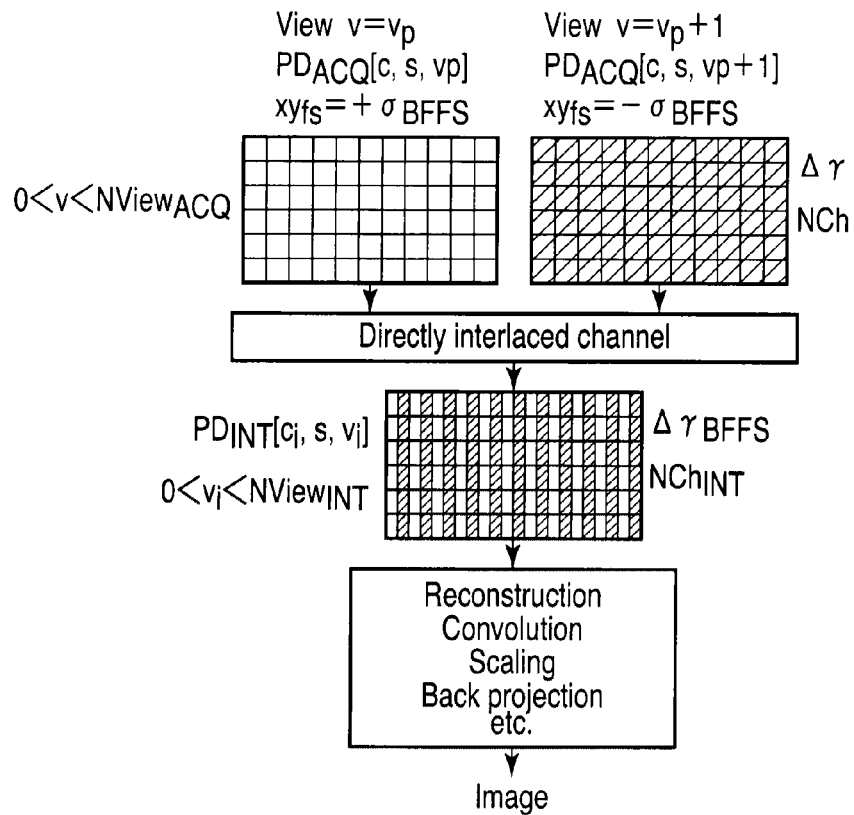
FIG. 5 is a view for explaining relocation by a projection data relocation unit in FIG. 1.

FIG. 5 shows a BFFS reconstruction sequence. Two acquired views $PD_{ACQ}[c, s, v_p]$ and $PD_{ACQ}[c, s, v_p+1]$ are interlaced (combined) in the channel direction into an interlaced view $PD_{INT}[c, s, v_i]$ corresponding to one channel. The size of each acquired original view is "(NSeg segment)×(NCh channel)", and the size of the view obtained by interlacing is "(Nseg)×(NCh$_{INT}$)".

$$NCh_{INT} = \frac{NCh}{2} \tag{16}$$

$$\Delta\gamma_{BFFS} = \frac{\Delta\gamma}{2} \tag{17}$$

$$v_i = \frac{v_p}{2} \tag{18}$$

The total number of views after interlacing is given by $$NView_{INT} = \frac{NVIEW_{ACQ}}{2} \tag{19}$$

where $NView_{ACQ}$ is the total number of views acquired.

In this embodiment, a view is reconstructed by using the cone beam Feldkamp algorithm. In other embodiments, it suffices to use different reconstruction algorithm. Channel interlacing is executed in a step after acquisition and before the reconstruction block in FIG. 5 including all other steps associated with general reconstruction, such as convolution and scaling. In another embodiment, channel interlacing can be performed in another step in a sequence of processing.

(Formation of Pair of Views to Be Interlaced)

Figure 6:
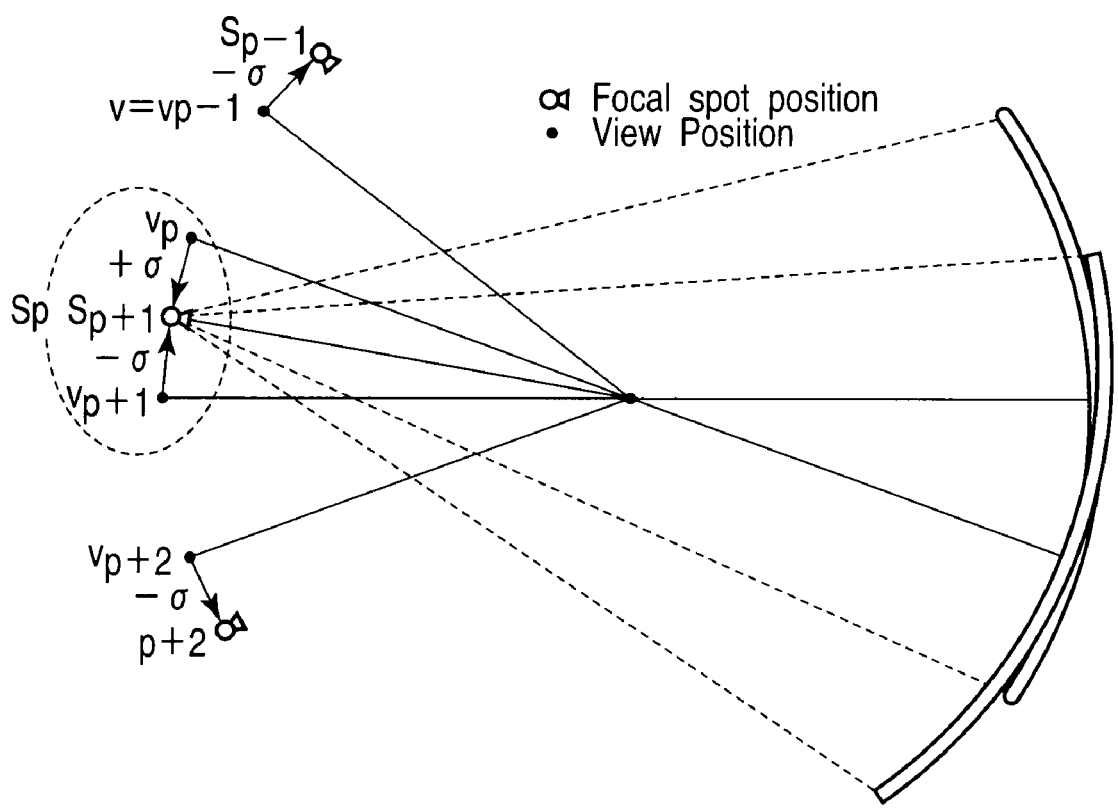
FIG. 6 is a view for explaining FIG. 2 in detail.

Views are not allowed to be arbitrarily interlaced. Only a pair of views obtained when the X-ray tube is at the same position are allowed to be interlaced, as shown in FIG. 6. In this embodiment, the X-ray tube position in the view $v_p+1$ is the same as that in the view $v_p$ (different from that in a view $v_p-1$), and the pair of views $v_p$ and $v_p+1$ are those which are always interlaced.

(Directly Interlaced Channels)

Figure 7:
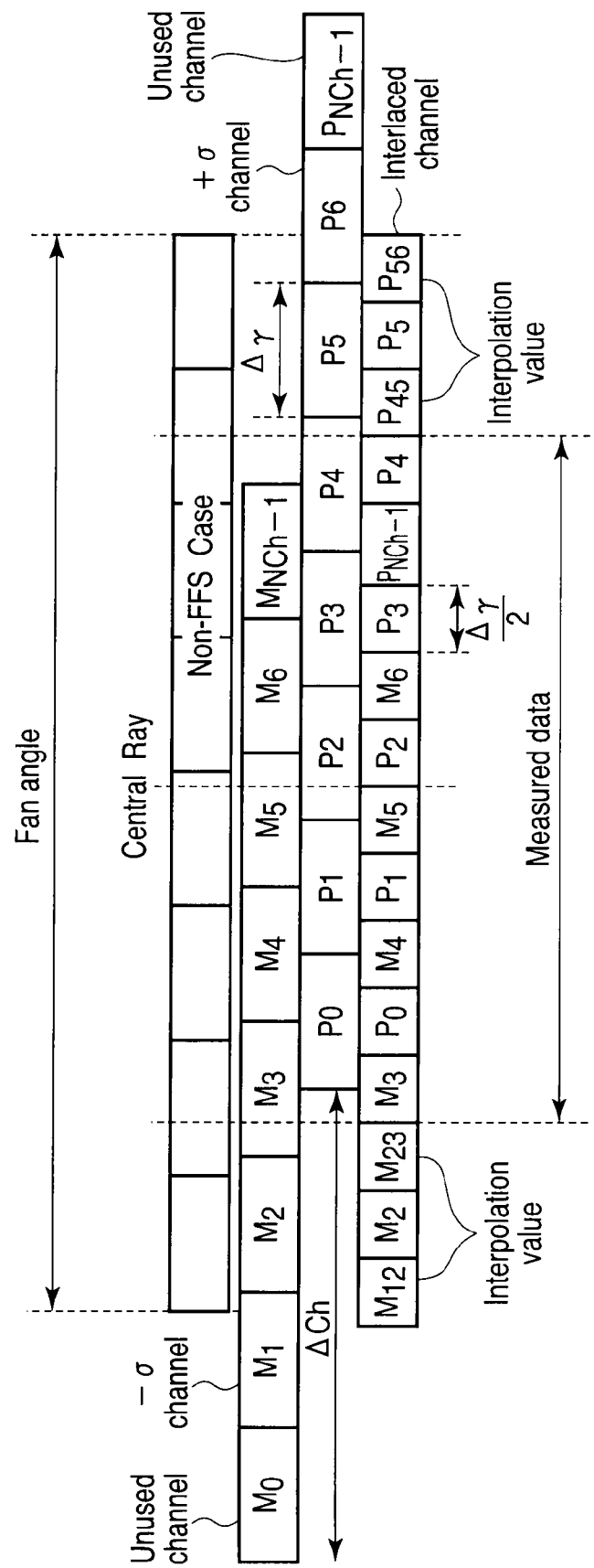
FIG. 7 is a view for explaining the contents of interpolation processing by a data interpolation unit in FIG. 1.
Figure 8:
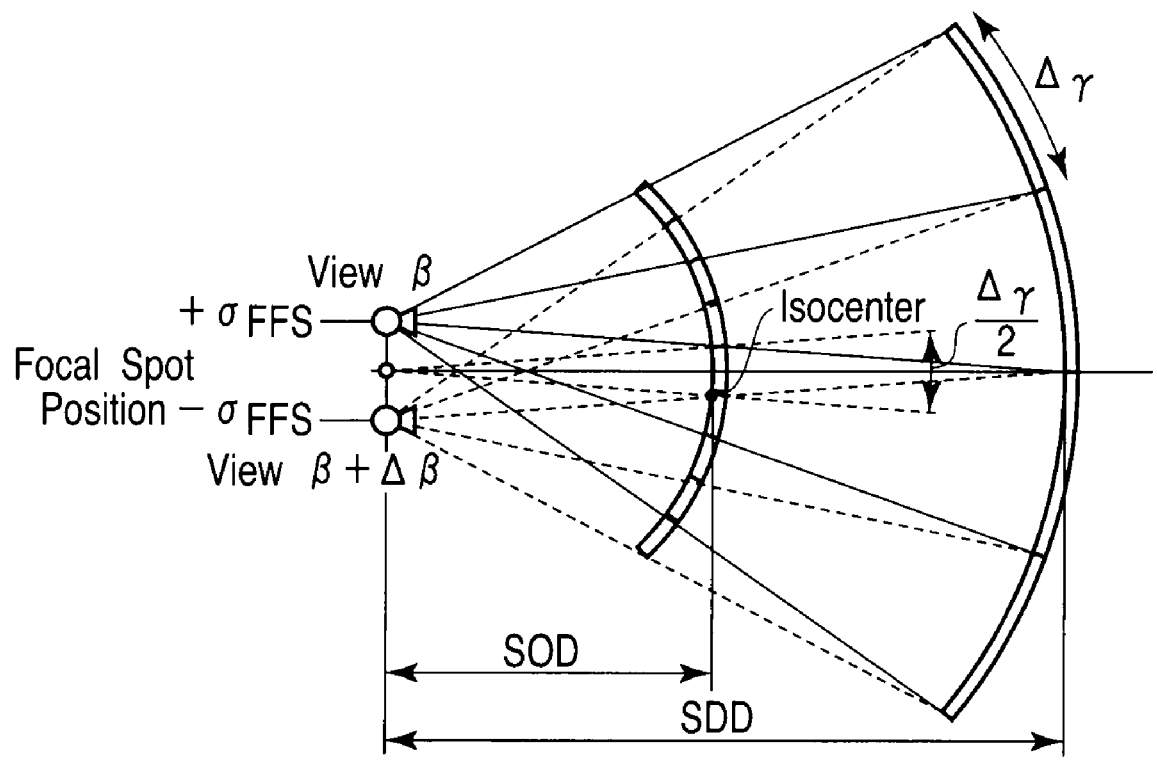
FIG. 8 is a view for explaining a conventional flying focal spot technique.

FIG. 7 shows the details of a directly interlaced channel box based on FIG. 5. Reference symbol P denotes a channel sequence corresponding to the view $v_p$; and M, a channel sequence corresponding to the view $v_p+1$, with each "single-digit subscript number" representing a channel number, and each "two-digit subscript number" representing the average between two channels corresponding to the subscript numbers. In this embodiment, an output array to be interlaced is interlaced so as to have the same fan angle as that of inputs. In another embodiment, when all channels are used, the output fan angle may be larger than the input fan angle. In accordance with the value of a shift amount ΔCh between channels, there are generated a complete data area in which channels corresponding to +σ and −σ overlap each other and an incomplete data area in which they do not overlap each other. A portion omitted from interlaced channels is interpolated by using the average between two adjacent values in the omitted channel. In the case shown in FIG. 6, since $P_{-1}$ does not exist, a value $M_{23}$ of an omitted channel is interpolated by averaging $M_2$ and $M_3$.

The following are equations for channel interlacing:

$$PD_{INT}[2c+IPO, s, v_i] = P[c, s]$$

$$0 \leq c \leq Ich \ldots \tag{20a,b}$$

$$PD_{INT}[2c+IMO, s, v_i] = M[c+IMI, s]$$

Channels to be interpolated are given by $$PD_{INT}[2k + APO, s, v_i] = \frac{P[k + API, s] + P[k + API + 1, s]}{2} \tag{21a, b}$$

$$0 \leq k < Ach$$

$$PD_{INT}[2k + AMO, s, v_i] = \frac{M[k + AMI, s] + M[k + AMI + 1, s]}{2}$$

where P and M respectively correspond to a view obtained by adding σ to the same X-ray tube position and a view obtained by subtracting o from the same X-ray tube position.

$$P[c, s] = PD_{ACQ}[c, s, v_p] \tag{22a, b}$$

$$M[c, s] = PD_{ACQ}[c, s, v_p + 1] \tag{23}$$

$$v_p = 2v_i$$

$$IMI = \text{int}\left(\frac{\Delta + 1}{2}\right) \tag{24}$$

$$IMO = \Delta \% 2 \tag{25}$$

$$ICh = NCh - IMI \tag{26}$$

$$IPO = \Delta + 1 \tag{27}$$

$$\Delta = \text{int}(\Delta Ch) \tag{28}$$

$$AMI = \text{int}\left(\frac{\Delta}{2}\right) \tag{29}$$

$$AMO = (\Delta + 1) \% 2 \tag{30}$$

$$ACh = \text{int}\left(\frac{\Delta + 1}{2}\right) \tag{31}$$

$$API = NCh - \Delta - 1 \tag{32}$$

$$APO = 2NCh - \Delta \tag{33}$$

(Modifications)

1) In this embodiment, the bent detector is incorporated in the conical beam arrangement. In another embodiment, a detector having a flat shape or another shape may be included in a non-conical beam arrangement such as a parallel arrangement.

2) In this embodiment, an output array to be interlaced is interlaced so as to have the same fan angle as that of inputs. In another embodiment, however, when all channels are to be used, the output fan angle may be larger than the input fan angle.

3) In this embodiment, the positive focal spot position +σ is in the same direction as the rotating direction of the gantry (i.e., +β). In another embodiment, however, the positive and negative directions can be defined in different manners.

4) In this embodiment, channel interlacing is performed immediately after data acquisition and before a reconstruction step such as convolution (see FIG. 4). In another embodiment, channel interlacing can be performed in a different part of the sequence of reconstruction processing, e.g., after convolution.

5) In order to simplify BFFS derivation, it is assumed that the degree of bend in the detector and the detector inclination can be neglected. In another embodiment, however, a BFFS can be derived without such assumptions.

Note that the present invention is not limited to the above embodiments, and constituent elements can be variously modified and embodied at the execution stage within the spirit and scope of the invention. Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus characterized by comprising:

an X-ray tube which generates X-rays;

a multi-channel X-ray detector which detects X-rays transmitted through an object to be examined;

a rotating frame which is equipped with the X-ray tube and the X-ray detector;

a reconstruction unit which reconstructs an image on the basis of an output from the X-ray detector; and a control unit which alternately shifts an X-ray focal spot of the X-ray tube along a rotating direction on an anode by a distance +σ and a distance −σ for each view, wherein the distance σ is set to $$\sigma = SOD \cdot \tan\left(\frac{\Delta\beta}{2}\right) \quad (5)$$

where SOD is a distance between the X-ray tube and a rotation center, and $\Delta\beta$ is an angle difference between adjacent views seen from the rotation center, such that X-ray focal spots in the adjacent views overlap each other at substantially the same position.

2. The apparatus according to claim 1, characterized by further comprising a relocation unit which relocates projection data of the adjacent views into projection data of a single view.

3. The apparatus according to claim 1, characterized in that the angle difference $\Delta\beta$ between the adjacent views is determined on the basis of an X-ray spread angle $\Delta\gamma$ corresponding to one channel of the X-ray detector.

4. The apparatus according to claim 1, characterized in that the X-ray tube generates a cone beam, and the X-ray detector is of a two-dimensional array type for receiving the cone beam.

5. The apparatus according to claim 1, characterized in that the control unit can change the number of views per rotation in accordance with a rotational speed of the X-ray tube.

6. An X-ray computed tomography apparatus characterized by comprising:
an X-ray tube which generates X-rays;
an X-ray detector in which detection elements which detect X-rays transmitted through an object to be examined are arranged for a plurality of channels;
a rotating frame which supports the X-ray tube and the X-ray detector;
a reconstruction unit which reconstructs an image on the basis of an output from the X-ray detector; and
a control unit which shifts an X-ray focal spot of the X-ray tube along a rotating direction on an anode so as to set the X-ray focal spot at substantially the same position in different views,
wherein the control unit is configured to change a shift amount of the X-ray focal spot in accordance with a rotational speed of the X-ray tube.

7. An X-ray computed tomography apparatus characterized by comprising:
an X-ray tube which generates X-rays;
an X-ray detector in which detection elements which detect X-rays transmitted through an object to be examined are arranged for a plurality of channels;
a rotating frame which supports the X-ray tube and the X-ray detector;
a control unit which shifts an X-ray focal spot of the X-ray tube along a rotating direction on an anode so as to set the X-ray focal spot at substantially the same position in different views;
projection data relocation means for obtaining projection data smaller in pitch than the detection elements of the X-ray detector on the basis of projection data of different views in which the X-ray focal spot is at substantially the same position; and
a reconstruction unit which reconstructs an image on the basis of projection data relocated by the projection data relocation means,
wherein the projection data relocation means comprises
first means for generating projection data with a fine pitch from projection data of two different views, and
second means for generating projection data with a fine pitch by performing interpolation processing for projection data of one view.

8. The apparatus according to claim 7, characterized in that the projection data relocation means relocates projection data so as to use projection data obtained by the first means near a center of the X-ray detector in a channel direction and use projection data obtained by the second means near an end of the X-ray detector in the channel direction.

* * * * *